United States Patent
Shan et al.

(10) Patent No.: US 10,183,161 B2
(45) Date of Patent: Jan. 22, 2019

(54) MICROLEAD FOR MULTIPOINT NEUROMODULATION OF THE CENTRAL NERVOUS SYSTEM

(71) Applicant: SORIN CRM SAS, Clamart (FR)

(72) Inventors: Nicolas Shan, Juvisy sur Orge (FR); The-hoa Lai, Courdimanche (FR)

(73) Assignee: Sorin CRM SAS, Clamart (FR)

( * ) Notice: Subject to any disclaimer, the term of this patent is extended or adjusted under 35 U.S.C. 154(b) by 0 days.

(21) Appl. No.: 15/947,755

(22) Filed: Apr. 6, 2018

(65) Prior Publication Data
US 2018/0221652 A1   Aug. 9, 2018

Related U.S. Application Data

(63) Continuation of application No. 15/044,927, filed on Feb. 16, 2016, now Pat. No. 9,937,340.

(30) Foreign Application Priority Data

Feb. 17, 2015 (FR) .................................... 15 51295

(51) Int. Cl.
| | |
|---|---|
| *A61N 1/00* | (2006.01) |
| *A61N 1/05* | (2006.01) |
| *A61N 1/08* | (2006.01) |
| *A61N 1/36* | (2006.01) |

(52) U.S. Cl.
CPC ......... *A61N 1/0529* (2013.01); *A61N 1/0551* (2013.01); *A61N 1/08* (2013.01); *A61N 1/36064* (2013.01); *A61N 1/36067* (2013.01); *A61N 1/36071* (2013.01); *A61N 1/086* (2017.08)

(58) Field of Classification Search
CPC .... A61N 1/0551; A61N 1/08; A61N 1/36071; A61N 1/36069; A61N 1/36064
See application file for complete search history.

(56) References Cited

U.S. PATENT DOCUMENTS

| | | |
|---|---|---|
| 5,246,014 A | 9/1993 | Williams et al. |
| 6,216,045 B1 | 4/2001 | Black et al. |
| 2006/0089697 A1 | 4/2006 | Cross et al. |

(Continued)

FOREIGN PATENT DOCUMENTS

| | | |
|---|---|---|
| CN | 104274902 | 1/2015 |
| EP | 2 581 107 A1 | 4/2013 |

(Continued)

OTHER PUBLICATIONS

Preliminary Search Report for French Patent Application No. 1551295, dated Dec. 7, 2015, 2 pages.

*Primary Examiner* — Mallika D Fairchild
(74) *Attorney, Agent, or Firm* — Foley & Lardner LLP

(57) ABSTRACT

A microlead, of an overall diameter less than 0.5 mm, includes a plurality of at least eight conductor wires individually insulated and twisted together. Each conductor wire includes an electrically conductive core microcable and an insulation layer surrounding the core microcable and having at least one exposed area to form a detection/stimulation electrode of the microlead. The microlead further includes a central support structure shaped as a surface of revolution, which may be free of conductor wires and of central lumen. The conductor wires are configured in one or more layers of twisted peripheral conductor wires carried by the central support structure and circumferentially distributed thereon.

20 Claims, 3 Drawing Sheets

(56) References Cited

U.S. PATENT DOCUMENTS

| | | |
|---|---|---|
| 2006/0111768 A1 | 5/2006 | Wessman et al. |
| 2010/0057176 A1 | 3/2010 | Barker |
| 2012/0191167 A1 | 7/2012 | McDonald et al. |
| 2013/0018445 A1 | 1/2013 | Sakai et al. |
| 2013/0073022 A1 | 3/2013 | Ollivier |
| 2013/0096658 A1 | 4/2013 | Shan et al. |

FOREIGN PATENT DOCUMENTS

| | | |
|---|---|---|
| EP | 2 682 151 A1 | 1/2014 |
| EP | 2 719 422 A1 | 4/2014 |
| WO | WO-2007/115198 | 10/2007 |

MICROLEAD FOR MULTIPOINT NEUROMODULATION OF THE CENTRAL NERVOUS SYSTEM

CROSS-REFERENCE TO RELATED PATENT APPLICATIONS

This application is a continuation of U.S. patent application Ser. No. 15/044,927, filed Feb. 16, 2016, which claims the benefit of and priority to French Patent Application No. 1551295, filed Feb. 17, 2015, both of which are incorporated herein by reference in their entirety.

BACKGROUND

The invention relates to "active implantable medical devices" as defined by Directive 90/385/EEC of 20 Jun. 1990 of the Council of the European Communities.

It is more specifically related to a neuromodulation microlead operating by multipoint stimulation of the central nervous system.

A neuromodulation lead is typically designed to be implanted in the cerebral venous network in order to target specific areas of the brain to apply electrical neurostimulation pulses for treating certain pathologies such as Parkinson's disease, epilepsy, etc. These techniques are grouped under the general term deep brain stimulation (DBS). The purpose of the lead may also be to stimulate the spinal cord, in particular for the treatment of pain. These techniques are known under the general name spinal cord stimulation (SCS).

These techniques differ in many aspects, including the methods used, from those employed in cardiology or in other types of nerve stimulation where the peripheral nervous system is stimulated, as in techniques known as vagus nerve stimulation (VNS) or analog techniques, where the electrodes are placed next to nerves or muscles, consequently in much more easily accessible areas.

The specificity of the leads for the stimulation of the central nervous system may results in the diameter of these leads being less than 1.5 French, or 0.5 mm, as well as having a lower number of electrodes to allow "multipoint" stimulation.

According to exemplary embodiments, the present disclosure provides a microlead structure that is able to reach deep brain areas in regions known as potentially effective in neuromodulation therapy, known under the name of the subthalamic nucleus (STN) or internal globus pallidus (GPI), and to precisely stimulate target areas located in these regions.

Current solutions of deep neurostimulation generally use a highly invasive approach, based on the perforation of the skull and on the implantation of the lead with an external guiding.

However, it would be desirable to provide methods enabling a far less invasive approach, through a venous access, implementing techniques similar to those used for the microcatheterization of the brain, used in the context of interventional neuroradiology. Provided that the leads have a sufficiently small diameter structure and are able to navigate in the venous and arterial system of the brain, these techniques could be used for the implantation of a microlead. In some implementations, the microlead must, however, remain suitable for permanent implantation in the brain.

Known microleads, however, face several major challenges using these methods.

First, leads of a too large diameter can cause severe neurological damage during the surgical implantation procedure. It is therefore necessary to greatly reduce the diameter of the microlead, while keeping its excellent maneuverability properties within the venous system to enable its implantation.

The cerebral arterial venous network includes high tortuosity and many branches, and it is essential to avoid trauma that a too rigid lead could provoke. But, conversely, too soft a microlead would be difficult to implant, due to a too low torsional stiffness to allow transmission of a rotation movement given from the proximal end over the entire length of the lead body until the distal end, (lack of "torquability"). Furthermore, a microlead that is too soft could not progress in the biological network without jamming under the effect of an axial thrust (lack of "pushability").

Second, it is desirable that the implantable lead is compatible with the catheters of 1.6 French (0.53 mm) such as those already used today in interventional neuroradiology, for example for the delivery of devices such as springs (coils) during the treatment of intracranial aneurysms. This implies a lead having an overall diameter of less than 1.5 French (0.5 mm).

Third, the electrodes of a neurostimulation microlead should have an extremely small surface, so as to specifically stimulate targeted areas without the risk of producing serious psychiatric side effects, which unfortunately occurs today in a significant percentage of interventions.

Finally, it is desirable to have a very high number of neurostimulation electrodes on the same microlead, all being independently selectable, so as to refine the accuracy of the stimulated contact points. In some embodiments, the microlead may have at least 8 (e.g., from 20 to 100) independently programmable electrodes, with the possibility to select electrodes located in different angular directions on the same longitudinal position of the lead. This multiplication of the number of electrodes, and consequently of the independent conductors, may be implemented without detriment to the small diameter of the microlead, which reduces its traumaticity and offers access opportunities to deep brain areas.

Various neuromodulation lead structures with multiple conductors have been proposed, for example in WO 2007/115198 A2, US 2006/0111768 A1 or US 2010/0057176 A1, but for a relatively small number of conductors, and consequently the number of programmable electrodes (on the order of ten at most).

US 2006/0089697 A1 discloses a lead including a plurality of independent stranded conductors, distributed around a hollow tube, the assembly being protected by an outer insulation jacket. The tube is traversed through by a central lumen for permitting insertion of a delivery stylet which is inserted into this lumen during implantation. The overall diameter of this structure (at least 0.8 mm) is, however, much too high to achieve the deepest target areas of the brain.

US2013/0018445 A1 discloses a neurostimulation lead having up to 49 conductor strands spirally wound and individually insulated, but in an application for stimulation of a peripheral nerve located in a muscle or in adipose tissue, which is in an environment where the constraints of a very small diameter and of navigability are not met.

EP 2581107 A1 and EP 2719422 A1 (Sorin CRM) describe implantable microleads structures in venous, arterial or lymphatic networks. These microleads however are primarily designed for implantation into the coronary venous network for stimulation of the myocardium left ventricle, therefore in cardiology applications. Their structure is specifically designed to withstand very severe fatigue stresses related to the heartbeat, which cause material fatigue as a result of repeated bending from hundreds of millions of cycles, which can cause the lead to break and limit the lifespan.

These issues are much less critical in the case of a DBS or SCS neuromodulation microlead, which is implanted in a more static environment than the heart and is much less prone to fatigue stresses. Moreover, multiplying the number of independent electrodes (e.g., at least 8, such as from 20 to 100) cannot be satisfied by the microleads structures described in these documents, which may include at most seven independent conductors within a diameter of 1.5 French (0.5 mm).

SUMMARY

Thus, according to various exemplary embodiments, the present disclosure aims at solving the problem by providing a specifically adapted multipoint stimulation microlead for the central nervous system, which may provide:

the possibility of increasing the number of conductors in a twisted structure which is compact, resistant to mechanical stress in bending and flexible, having up to 100 insulated wires in a dimension less than 0.5 mm;

the possibility of achieving, in this structure, very small electrodes, and oriented in a plurality of axial directions; and a microlead that is suited for long term implantation in permanent neurological stimulation applications after implantation in the cerebral venous network.

According to some embodiments, the disclosure provides a multipolar microlead with an overall diameter less than 1.5 French (0.5 mm) including at least eight conductor wires individually insulated and twisted together. Each conductor wire includes a microcable having an electrically conductive core, connected in the proximal portion to a pole of a generator of an active implantable medical device; and an insulation layer surrounding the core cable and having at least an exposed zone formed in the thickness of the insulation layer in the distal portion to form a detection/stimulation electrode of the microlead.

In some embodiments, the microlead further includes a central support structure having a revolution surface shape, the central support structure being free of i) conductor wires and of ii) central lumen, and the conductor wires are configured in a layer of a twisted coil of peripheral conductor wires carried by the central support structure and circumferentially distributed thereon.

According to various embodiments:

a portion of the peripheral conductor wires are configured in a first layer directly carried by the central support structure and another part of the peripheral conductor wires are configured in a second layer carried by the first layer;

the central support structure includes a single homogeneous cylindrical element with a solid or tubular section, or a plurality of homogeneous cylindrical elements stranded together, with a solid or tubular section;

the central support structure includes a coil of a circuit protecting against excess current induced during MRI examination;

the overall diameter of the central support structure is greater than the diameter of an individual conductor wire;

against bending stresses, the central support structure has a capacity for elastic deformation higher than that of all the individual conductor wires;

the central support structure is a tapered structure with a decreasing diameter from the proximal region to the distal region including a structure including a conical transition portion between a proximal cylindrical portion of greater diameter than that of the nominal unit diameter of an individual conductor wire, and a cylindrical distal portion of smaller diameter than the proximal portion;

the plurality of conductor wires include from 10 to 50 conductor wires by layer; and the unit diameter of an individual conductor wire is between 15 and 25 µm.

BRIEF DESCRIPTION OF THE DRAWINGS

Further features, characteristics and advantages of the present disclosure will become apparent to a person of ordinary skill in the art from the following detailed description of preferred embodiments of the present invention, made with reference to the drawings annexed, in which like reference characters refer to like elements and in which.

DETAILED DESCRIPTION

Various exemplary embodiments of the disclosure will now be described.

Figure 1:
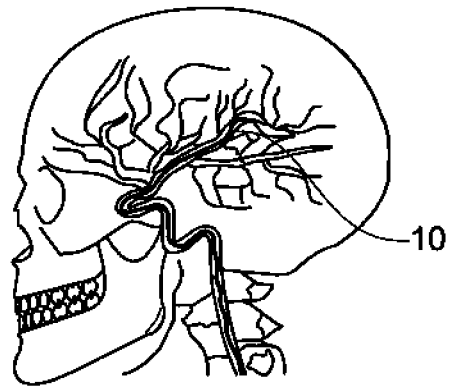
FIG. 1 generally illustrates an exemplary implantation of a microlead in the cerebral vasculature according to an embodiment of the disclosure.

In FIG. 1, a microlead 10 according to an exemplary embodiment, the disclosure is generally illustrated, implanted in the cerebral vasculature to selectively stimulate deep brain areas by localized application of electrical pulses. The electrodes of the microlead may also act as, where appropriate, detection electrodes to collect electrical potentials produced locally.

Stimulation of target areas of the brain involves implementation of neuromodulation techniques for treating pathologies such as Parkinson's disease, epilepsy and other neurological diseases.

Consequently, in some implementations, it is necessary to access deep brain regions, which are difficult to reach today with the known techniques.

Stimulation microleads for this purpose should not only have great solidity, so as to ensure long term biostability (these microleads may be intended to be permanently implanted), but also a very small size (e.g., with an overall diameter less than 1.5 French (0.5 mm)). In particular, these 1.5 French microleads would be advantageously compatible with 1.6 French (0.53 mm) catheters, which are already used in interventional neuroradiology, for example, for the release of devices such as coils for the treatment of intracranial aneurysms.

In some embodiments, these microleads bear a high number of electrodes (e.g., from 20 to 100 electrodes), which may be independently selectable so as to very precisely choose the stimulation zones according to the desired effect. It is also desirable to be able to select the axial direction in which these electrodes act, so as to optimize the resulting effect and to avoid undesirable side effects.

Figure 2A:
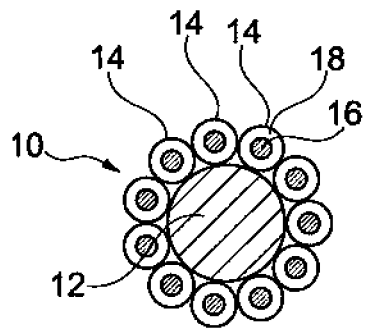
FIGS. 2a and 2b show in cross section and in side view respectively, the overall structure of the microlead according to an embodiment of the disclosure.
Figure 2B:
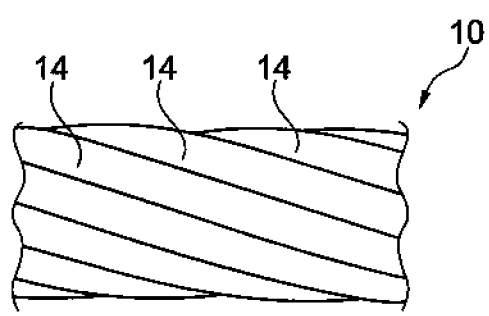

FIGS. 2a and 2b show the microlead structure proposed by the present disclosure in section view and in side view, respectively, according to an exemplary embodiment.

The microlead 10 includes a central support structure 12 with a revolution surface shape (i.e., a shape generated by revolving a straight line or a curve around an axis), covered on its periphery by a plurality of peripheral conductor wires 14 carried by the central support structure 12 and circumferentially spread thereof.

Each of these peripheral conductor wires 14 includes an electrically conducting core microcable 16 and an insulation layer 18 surrounding the core microcable.

The core microcable can be made of a conductor metal such as a Platinum-Iridium alloy, a MP35N steel, Nitinol, etc. Various core microcable structures appropriate for this application are in particular disclosed in the EP2581107 A1 (Sorin CRM) cited above, which can be referred to for further details. It is also possible to use materials such as carbon nanotubes for the core microcable 16, which are materials with exceptional mechanical resistance and with very good electrical conductivity characteristics.

For the insulation layer 18, materials such as polyurethanes (PU), polyester (PET), polyamides (PA), polycarbonates (PC), polyimides, fluoropolymers, polyether ether ketone (PEEK), poly-p-xylylene (parylene), or polymethyl methacrylate (PMM). However, preference may be given to high chemical inertia materials such as fluoropolymers, which also have a very good insulation, particularly PTFE (polytetrafluoroethylene), FEP (perfluorinated propylene), PFA (perfluoroalkoxy copolymer resin), THV (tetrafluoroethylene, hexafluoropropylene, vinylidene fluoride), PVDF (polyvinylidene fluoride), EFEP (ethylene fluorinated ethylene propylene), or ETFE (ethylene tetrafluoroethylene) may be used.

Each of the conductor wires is present in the distal region of the lead in at least one exposed area (as shown at 38 or 38' in FIG. 6) formed in the thickness of the insulation layer, forming a detection/stimulation electrode of the microlead.

The architecture of the microlead according to an exemplary embodiment of the disclosure, with a twisted coil of isolated peripheral conductor wires 14 carried by a central support structure 12, reduces the size of the lead in very large proportions while providing a large number of insulated electrical lines, connected to independent and therefore programmable electrodes according to multiple configurations of the generator to which the microleads are connected.

Preferably, to minimize its size, this structure does not include a central lumen (a channel opening at both ends of the lead), so for the implantation of the microlead, the guiding is done externally via a delivery catheter, and not by a guidewire inserted into a central lumen.

Figure 3A:
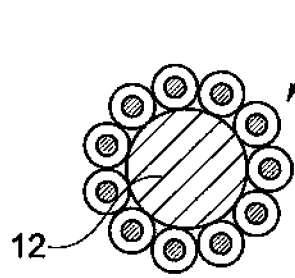
FIGS. 3a to 3d illustrate various embodiments of the central support structure of the microlead according to an embodiment of the disclosure.
Figure 3B:
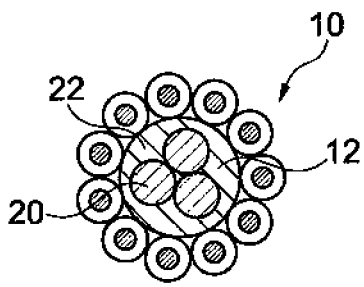
Figure 3C:
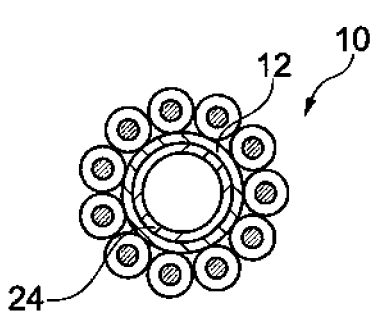

FIGS. 3a to 3d illustrate various embodiments of the central support structure 12:

FIG. 3a: a simple core, formed of a homogeneous single strand nucleus;

FIG. 3b: a core of a multi-strand nucleus, with several strands 20 embedded in a coating 22;

FIG. 3c: a tubular core 24; and

Figure 3D:
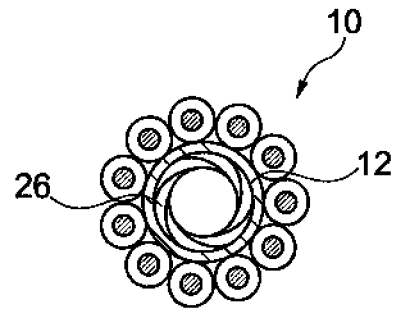

FIG. 3d: a support structure incorporating in its core a coil 26 of a circuit protecting against excess current induced in MM examination situation.

The materials of the central support structure 12 may be selected and/or combined depending on the desired final properties for the microlead, so as to provide the microlead with multiple features such as:

radiopacity, by incorporation of a metal such as tantalum, palladium, gold or a platinum-iridium alloy in the material of the central support structure 12;

shape memory, by use of polymers with properties of flexibility and high elastic performance such as PEEK, PA, PEBA, PU, PET or PFE; and flexibility, "pushability" and "torquability". The central support structure 12 may present, against bending stresses, a capacity for elastic deformation which is greater than that of the individual conductor wires 14, this ability to the bending deformation being required to go in the deep brain network.

Figure 4:
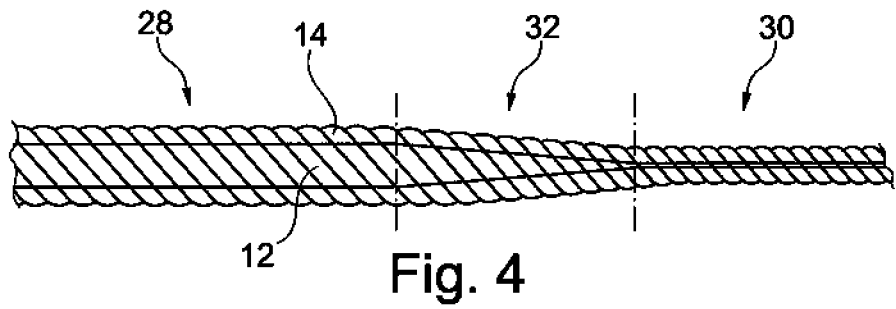
FIG. 4 illustrates a particular embodiment of a microlead, with a central support structure having a conical portion.

As shown in FIG. 4, to further improve the performances of the microlead during implantation, in particular the ability to advance lengthwise and crosswise without jamming, it is possible to provide a cylindrical proximal portion 28 of a nominal diameter, connected to a distal portion 30 smaller in diameter via a conical transition portion 32. The proximal portion 28 of larger diameter provides the "pushability", that is to say the ability of advancing the microlead under the effect of axial stress applied for example by an operating handle from the proximal end, while the much thinner distal portion 30 enables the microlead to easily reach deep, narrow, vessels of the brain region.

Figure 5:
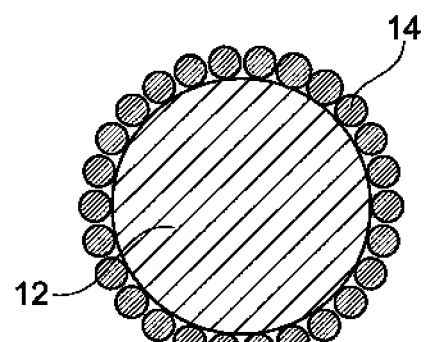
FIG. 5 illustrates, in cross section, an embodiment of a microlead according to the disclosure with twenty-six electrodes.

FIG. 5 illustrates an embodiment of a microlead according to the disclosure with twenty-six electrodes, thus including twenty-six peripheral conductor wires 14 carried by a central support structure 12.

The highly compact structure allows the use of insulated wires which can have a diameter as small as 15-25 µm. Therefore it is possible to place up to fifty conductor wires, and thus have as much independent electrodes in an overall diameter of 0.40 mm for a unit wire conductor diameter of 25 µm (the number of conductors wires geometrically increasing by reducing the size of the conductors).

Figure 6:
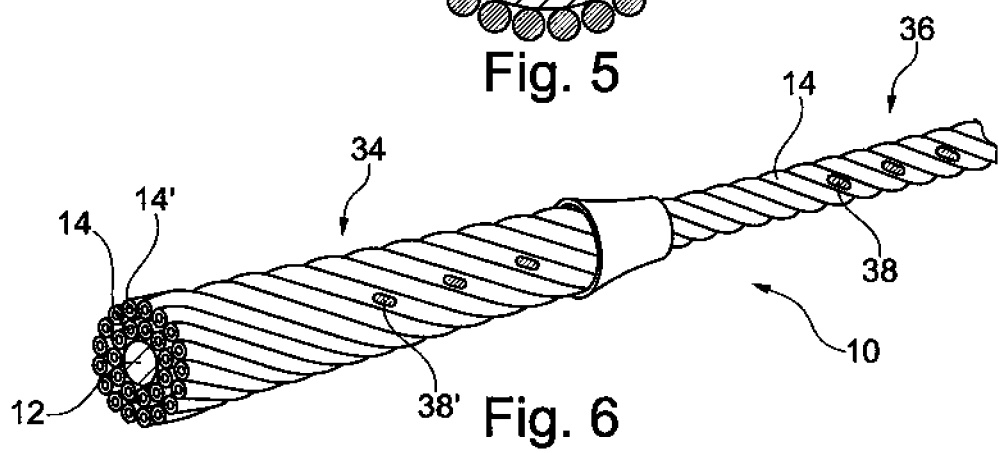
FIGS. 6 and 7 show an embodiment of the microlead in side view and in cross section, including two layers of superimposed peripheral conductors, respectively.
Figure 7:
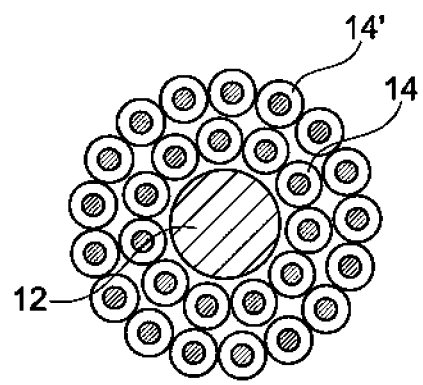

FIGS. 6 and 7 illustrate a variant including two superimposed layers of conductors on the central support structure, with a first layer of peripheral conductor wires 14 directly carried by the central support structure 12, and a second layer of peripheral conductor wires 14' carried by the first conductor layer 14. It is possible to independently operate all the structural layers and thus increase the possibilities with up to over a hundred conductors 14 or 14' independently operable even in a structure in which the overall diameter does not exceed 0.5 mm. The two layers of respective conductor wires 14 and 14' can be axially displaced, with a proximal zone 34 where the second conductive layer 14' is visible, and a distal region 36 where the surface of conductors 14 of the first layer is visible. The proximal region 34 carries the electrodes 38' connected to the conductors 14', while the distal region 36 carries the electrodes 38 connected to the conductors 14.

Figure 8:
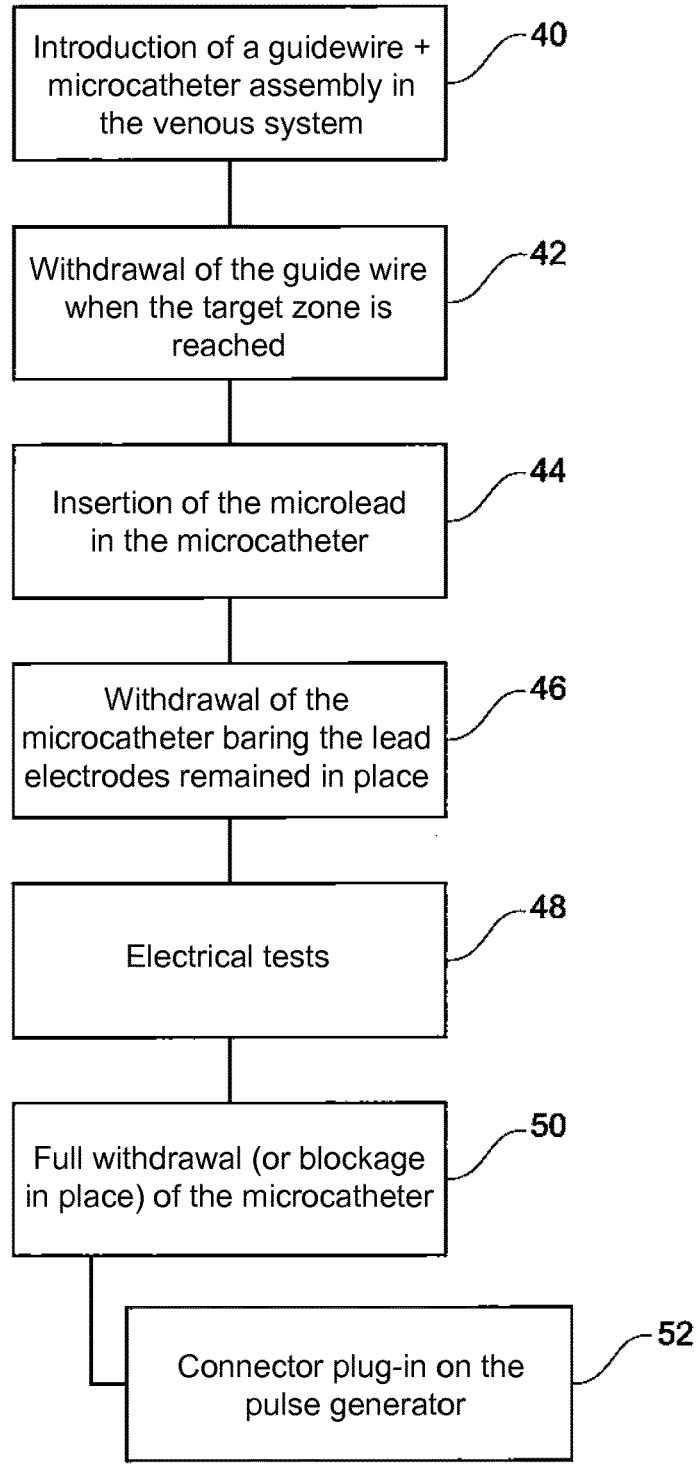
FIG. 8 is a flow chart describing the various steps of an implantation procedure of a microlead according to an exemplary embodiment of the disclosure.

FIG. 8 schematically shows the different phases of the implantation method of the lead as described above.

This method is similar to that of a conventional lead, apart from the fact that due to the lack of internal lumen, it is not possible to use a guidewire to introduce the lead for guiding it in the vessels of the cerebral network. It is then preferred to use a microcatheter instead, according to procedures known by practitioners.

The first step (block 40) consists of introducing an assembly of a microcatheter and a guidewire into the venous system up to the target area.

When the target area has been reached (block 42), the guidewire is withdrawn, leaving in place the microcatheter.

The microlead is then introduced into the microcatheter (block 44), then the microcatheter is partially removed to gradually discover the electrodes of the microlead (block 46).

Electrical tests are then automatically or manually carried out (block 48). Once these tests are done, and it is confirmed that the lead is fully functional, the microcatheter is completely removed (block 50), or locked in place if it is a microcatheter that can be permanently implanted as described, for example, in EP 2 682 151 A1 (Sorin CRM).

The lead connector can then be connected to the pulse generator (block 50) so that it can deliver neurostimulation pulses to the brain.

What is claimed is:

1. A microlead for implantation in a cerebral venous system, comprising:
   a central support structure shaped in the form of a surface of revolution; and
   at least eight conductor wires individually insulated and twisted together, each conductor wire comprising:
      an electrically conductive core microcable comprising a proximal portion and a distal portion, the proximal portion structured to connect to a pole of a generator of an active implantable medical device;
      an insulation layer surrounding the core microcable; and
      an exposed area formed in the insulation layer at the distal portion of the core microcable, the exposed area exposing a portion of the core microcable and forming an electrode of the microlead,
   the at least eight conductor wires arranged to form:
      a first layer of conductor wires twisted around the central support structure;
      a second layer of conductor wires twisted around the first layer of conductor wires on at least a proximal portion of the microlead;
      a proximal zone where the second layer of conductor wires are exposed to an exterior portion of the lead; and
      a distal zone where the first layer of conductor wires are exposed to the exterior portion of the lead,
   wherein the lead has an outer diameter less than 0.5 millimeters.

2. The microlead of claim 1, wherein the lead is lumenless.

3. The microlead of claim 1, wherein the central support structure comprises a single homogeneous cylindrical element of solid or tubular section.

4. The microlead of claim 1, wherein the central support structure comprises a plurality of homogeneous cylindrical elements of solid or tubular sections stranded together.

5. The microlead of claim 1, wherein the central support structure comprises a coil of a protection circuit protecting against over-current induced during an MRI.

6. The microlead of claim 1, wherein an overall diameter of the central support structure is greater than a diameter of an individual conductor wire.

7. The microlead of claim 1, wherein, in response to bending stresses, the central support structure has a capacity for elastic deformation higher than that of all the conductor wires.

8. The microlead of claim 1, wherein the at least eight conductor wires comprises 10 to 50 conductor wires in the first and second layers of conductor wires.

9. The microlead of claim 1, wherein the individual diameter of each conductor wire is between 15 and 25 μm.

10. The microlead of claim 1, wherein the electrodes of the at least eight conductor wires are independently selectable.

11. The microlead of claim 1, wherein an axial direction that the electrodes of the at least eight conductor wires are acting can be selected.

12. The microlead of claim 1, wherein the microlead is structured to be implanted using a microcatheter.

13. An implantable medical device, comprising:
   a generator structured to provide electrical stimulation; and
   a multipolar microlead for implantation in a cerebral venous system, comprising:
      a central support structure shaped in the form of a surface of revolution; and
      at least eight conductor wires individually insulated and twisted together, each conductor wire comprising:
         an electrically conductive core microcable comprising a proximal portion and a distal portion, the proximal portion structured to connect to a pole of a generator of an active implantable medical device;
         an insulation layer surrounding the core microcable; and
         an exposed area formed in the insulation layer at the distal portion of the core microcable, the exposed area exposing a portion of the core microcable and forming an electrode of the microlead,
      the at least eight conductor wires arranged to form:
         a first layer of conductor wires twisted around the central support structure;
         a second layer of conductor wires twisted around the first layer of conductor wires on at least a proximal portion of the microlead;
         a proximal zone where the second layer of conductor wires are exposed to an exterior portion of the lead; and
         a distal zone where the first layer of conductor wires are exposed to the exterior portion of the lead,
      wherein the lead has an outer diameter less than 0.5 millimeters.

14. The implantable medical device of claim 13, wherein the lead is lumenless.

15. The implantable medical device of claim 13, wherein the central support structure comprises a single homogenous cylindrical element of solid or tubular section.

16. The implantable medical device of claim 13, wherein the central support structure comprises a plurality of homogeneous cylindrical elements of solid or tubular sections stranded together.

17. The implantable medical device of claim 13, wherein the central support structure comprises a coil of a protection circuit protecting against over-current induced during an MRI.

18. The implantable medical device of claim 13, wherein an overall diameter of the central support structure is greater than a diameter of an individual conductor wire.

19. The implantable medical device of claim 13, wherein, in response to bending stresses, the central support structure has a capacity for elastic deformation higher than that of all the conductor wires.

20. The implantable medical device of claim 13, wherein the at least eight conductor wires comprises 10 to 50 conductor wires in the first and second layers of conductor wires.

* * * * *